United States Patent
Zhang et al.

(10) Patent No.: US 10,046,289 B2
(45) Date of Patent: Aug. 14, 2018

(54) METHOD FOR REPLACEMENT OF PHOSGENE SYNTHESIS COLUMN CATALYST

(71) Applicant: WANHUA CHEMICAL GROUP CO., LTD., Yantai (CN)

(72) Inventors: Hongke Zhang, Yantai (CN); Yu Yao, Yantai (CN); Dongke Zhao, Yantai (CN); Guanyi Cao, Yantai (CN); Xiaogao Liu, Yantai (CN); Younian Cao, Yantai (CN); Chong Li, Yantai (CN); Yabo Ma, Yantai (CN)

(73) Assignee: Wanhua Chemical Group Co., Ltd., Shandong (CN)

( * ) Notice: Subject to any disclaimer, the term of this patent is extended or adjusted under 35 U.S.C. 154(b) by 0 days.

(21) Appl. No.: 15/536,425

(22) PCT Filed: Jan. 16, 2015

(86) PCT No.: PCT/CN2015/070863
§ 371 (c)(1),
(2) Date: Jun. 15, 2017

(87) PCT Pub. No.: WO2016/109987
PCT Pub. Date: Jul. 14, 2016

(65) Prior Publication Data
US 2017/0348661 A1    Dec. 7, 2017

(30) Foreign Application Priority Data
Jan. 7, 2015 (CN) .......................... 2015 1 0007425

(51) Int. Cl.
*B01J 8/06* (2006.01)
*B01J 8/00* (2006.01)
*B01J 27/20* (2006.01)
*C01B 32/80* (2017.01)

(52) U.S. Cl.
CPC ............ *B01J 8/06* (2013.01); *B01J 8/008* (2013.01); *B01J 27/20* (2013.01); *C01B 32/80* (2017.08); *B01J 2208/06* (2013.01)

(58) Field of Classification Search
CPC .................................. B01J 8/06; C01B 32/80
See application file for complete search history.

(56) References Cited

U.S. PATENT DOCUMENTS 4,064,218 A  * 12/1977  Scholz .................. B01D 53/70
                                                 423/240 R

FOREIGN PATENT DOCUMENTS

| CN | 101348446 A | 1/2009 |
|---|---|---|
| CN | 101829526 A | 9/2010 |
| CN | 202199338 U | 4/2012 |
| CN | 102502700 A | 6/2012 |
| CN | 103044286 A | 4/2013 |
| CN | 103073452 A | 5/2013 |
| CN | 103044286 B * | 4/2015 |
| FR | 1363868 A | 6/1964 |
| WO | 02/20468 A1 | 3/2002 |

OTHER PUBLICATIONS

International Search Report and Written Opinion dated Sep. 16, 2015, directed to International Application No. PCT/CN2015/070863; 19 pages.

* cited by examiner

Primary Examiner — Paul A Zucker

(57) ABSTRACT

The present invention discloses a method of quickly desorbing phosgene from a catalyst in a phosgene synthesizing tower when the catalyst in the phosgene synthesizing tower is replaced. The method is carried out by first purging out easily-desorbed phosgene from the catalyst activated carbon in the phosgene synthesizing tower with nitrogen gas, then purging with ammonia gas, and the ammonia gas is reacted with the hardly-desorbed phosgene in the catalyst of the phosgene synthesizing tower. Then the phosgene synthesizing tower is rinsed with a water gun and then dried with hot gas. The phosgene content at an outlet of the phosgene synthesizing tower after purging is below 0.5 ppm, which can significantly save the time of the phosgene synthesizing tower for purging the phosgene, greatly reduce the amount of nitrogen gas consumed, and improve the safety of the process operation.

15 Claims, 1 Drawing Sheet

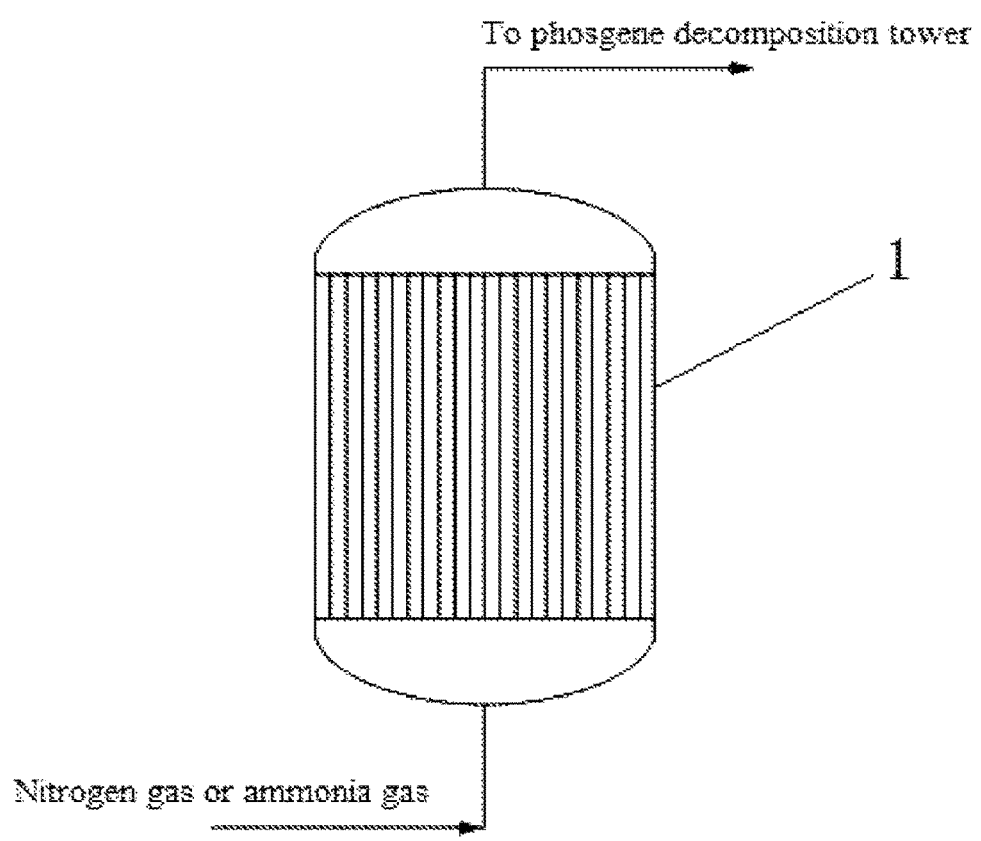

METHOD FOR REPLACEMENT OF PHOSGENE SYNTHESIS COLUMN CATALYST

FIELD OF THE INVENTION

The present invention relates to a method of replacing a catalyst in a phosgene synthesizing tower, in particular to a method of quickly desorbing phosgene from a catalyst for phosgene synthesis when the catalyst in the phosgene synthesizing tower is replaced.

BACKGROUND OF THE INVENTION

Phosgene is an important organic intermediate which is widely used in pesticides, pharmaceuticals, engineering plastics, polyurethane materials and military. Phosgene can be prepared with various methods. A primary method for industrial production of phosgene at present uses carbon monoxide and chlorine as raw materials, with activated carbon as a catalyst for the synthesis of phosgene wherein the commonly used activated carbon is cocoanut charcoal and coal-based charcoal. 80% of phosgene from industrial production is currently used for the production of isocyanates, mainly used for the production of MDI (diphenylmethane diisocyanate), TDI (toluene diisocyanate) and polycarbonate. Production of isocyanates has very strict requirements on the quality of the raw material phosgene, wherein a content of the free chlorine in the phosgene is controlled within 200 ppm, and 5-10% of CO excess relative to chlorine in industry is generally used to control the content of the free chlorine in the synthesized phosgene. At the late stage of phosgene synthesis, with pulverization of the catalyst activated carbon and decrease of the catalytic ability, the content of the free chlorine in the synthesized phosgene is increased, and the catalyst in the phosgene synthesizing tower need to be replaced.

Phosgene, as a highly toxic chemical, has an allowable maximum concentration of 0.5 ppm in the air. It is necessary to purge the phosgene remained in the synthesizing tower and adsorbed in the activated carbon, before replacing the activated carbon in the phosgene synthesizing tower. Activated carbon has a relatively large saturate adsorption rate on phosgene, and it takes a long time to purge so as to completely desorb the phosgene from the activated carbon, which prolongs the time for replacing the catalyst in the phosgene synthesizing tower, and it is also necessary to consume a lot of nitrogen gas.

Chinese Patent No. CN102502700A discloses a method of replacing a catalyst in an ammonia gas synthesis system. Described by the patent is that carbon dioxide gas is introduced into a synthesis system after the synthesis system is decompressed, the carbon dioxide gas is used to replace the gas in the system, which however, is less effective in desorbing a small amount of phosgene from the activated carbon, resulting in longer purging time finally.

Chinese Patent CN202199338U discloses a solid catalyst replacing apparatus. Described by the patent is to arrange a vacuum valve and a feed inlet at the top of the catalyst storage tank wherein the vacuum valve is connected to a vacuum pump via a vacuum tube and the feed inlet is communicated with reaction tubes packing the catalyst in the reactor via a feed pipe. However, the activated carbon in the phosgene synthesizing tower has a relatively large adsorption rate on the phosgene, and the outlet of the synthesizing tower requires an extremely low concentration of phosgene. It is difficult to completely remove the phosgene from the phosgene synthesizing tower directly through the vacuum system in a comparatively short time.

Chinese Patent No. CN101829526A discloses a catalyst replacing system, a catalyst replacing method, and a rectifying tower having the system. Described by the patent is that a catalyst is processed by a rectification system and then pumped to a reaction system. However, the phosgene synthesizing tower is a gas-solid reaction system, and the activated carbon cannot be regenerated after reaching its service life.

The method of replacing the catalyst in the synthesizing tower described by the above patent has disadvantages of long phosgene purging time and complicated device for catalyst replacement. It has not been reported any process for quickly purging the phosgene synthesizing tower so as to improve the catalyst replacement rate of the catalyst in the phosgene synthesizing tower. Therefore, in view of the characteristics of the phosgene synthesizing tower system and the nature of the phosgene, it is necessary to develop a method of quickly removing phosgene from the phosgene synthesizing tower with facilitating safe operation.

In the prior art, only nitrogen gas is used to directly purge the phosgene synthesizing tower, and it is necessary to consume a large amount of nitrogen gas when phosgene concentration is low in the later stage of purging, and the purging rate is very slow. Some of the phosgene remains in the synthesizing tower, and there are still great risks in replacing the catalyst in the synthesizing tower.

SUMMARY OF THE INVENTION

It is an object of the present invention to provide a method of replacing a catalyst (e.g., activated carbon) in a phosgene synthesizing tower, which can quickly remove phosgene from the phosgene synthesizing tower to 0.5 ppm or less by nitrogen purging, ammonia gas purging and optionally building the pressure with ammonia gas. This method can significantly reduce the time for replacing the catalyst in the phosgene synthesizing tower, the process flow is simple, the nitrogen gas consumption is reduced and the operation safety of the process is high.

In order to realize the above object, the present invention adopts the following technical solution:

According to a first embodiment of the present invention, provided is a method of quickly desorbing phosgene from a catalyst in a phosgene synthesizing tower before the catalyst in the phosgene synthesizing tower is replaced, comprising:

(A) purging with nitrogen gas: after feeding of carbon monoxide and chlorine to the phosgene synthesizing tower is discontinued, nitrogen gas is introduced into the bottom of the phosgene synthesizing tower for purging, the phosgene in the phosgene synthesizing tower is purged to a phosgene decomposition tower until the phosgene concentration at the outlet of the phosgene synthesizing tower is lower a specified level, i.e., measured as below 0.5% (v/v), preferably 0.05-0.5% (v/v), more preferably 0.1-0.45% (v/v) relative to the overall volume of gas;

optional B) building the pressure (pressure build-up): the outlet of the phosgene synthesizing tower is closed, the ammonia gas is introduced into the bottom of the phosgene synthesizing tower to build up the pressure of the phosgene synthesizing tower, and then the outlet of the phosgene synthesizing tower is opened to discharge gas from the phosgene synthesizing tower, wherein two operations including building up pressure and opening the outlet of the phosgene synthesizing tower are carried out once or several times repeatedly; and (C) purging with ammonia gas: ammonia gas is continuously introduced into the bottom of the phosgene synthesizing tower for purging.

Generally, it is impossible to reduce the phosgene concentration in the phosgene synthesizing tower to 0.5 ppm or less only by way of purging the phosgene with nitrogen gas, and furthermore, it needs at least 6 days to reduce the phosgene concentration at the outlet of the synthesizing tower to 0.1% by purging with nitrogen gas. If it is intended to further reduce the phosgene concentration, the rate of removing phosgene with nitrogen gas purging is significantly decreased and the purging time is greatly prolonged, because the phosgene is adsorbed in the pores of the activated carbon at the moment and the adsorption force is strong. For example, it takes up to 30 to 35 days to reduce the phosgene concentration to 8 to 10 ppm. Moreover, if the phosgene concentration is too high after purging with nitrogen gas, the amount of the ammonia gas needed is more as well, in addition, the amount of the ammonium chloride and urea powder produced are more, which will block the tubes of the synthesizing tower, resulting in higher pressure drop and pressure rise of the phosgene synthesizing tower. The phosgene concentration at the outlet of the phosgene synthesizing tower after purging with nitrogen gas is controlled to be in a range of from 0.05 to 0.5%, preferably from 0.1 to 0.45%.

In the early stage of introduction of ammonia gas, there is still relatively more phosgene in the phosgene synthesizing tower, in order to prevent the ammonia gas from being taken out of the synthesizing tower along with phosgene at the early stage to generate solids from reaction in the subsequent pipeline thereby block the pipeline, a pressure is built up for a certain time such that the phosgene is reacted with the ammonia gas, and then the ammonia gas is kept being introduced. Therefore, step (B) is preferred, and as such, the utilization of the ammonia gas can also be improved.

The phosgene synthesizing tower device according to the present invention may be any tube-type reactor known to those skilled in the art. A catalyst filling method known to those skilled in the art may be used for filling fresh catalyst to the phosgene synthesizing tower.

It is further preferred that the above-said method further comprises:

D) replacing the catalyst: taking out the catalyst (e.g., activated carbon) from the phosgene synthesizing tower and loading the fresh catalyst (e.g., activated carbon) therein.

It is preferred that, as for the case of using a tube-type phosgene synthesizing tower, the step D) of replacing the catalyst (e.g., activated carbon) is carried out by taking out the catalyst from the tubes of the phosgene synthesizing tower (e.g., poking the catalyst out from the tubes by separating the upper and lower seal heads of the phosgene synthesizing tower), and then rinsing the tubes of the phosgene synthesizing tower using water gun, and drying the synthesizing tower tube with hot gas, and then filling the fresh catalyst (for example, activated carbon) into the tubes of the synthesizing tower.

Preferably, in step (A), the temperature of nitrogen gas for purging is from 80 to 160° C., preferably from 100 to 150° C. The moisture content in the nitrogen gas is 500 ppm or less, preferably from 30 to 500 ppm, more preferably from 50 to 300 ppm.

Preferably, in step A), the flow of nitrogen gas for purging is from 50 to 500 Nm$^3$/h, preferably from 100 to 400 Nm$^3$/h. The time for purging with nitrogen gas is from 1 to 10 days, preferably from 2 to 6 days. The pressure of nitrogen gas for purging is from 0.05 to 1.0 MPa, preferably from 0.102 to 0.3 MPa, more preferably from 0.15 to 0.25 MPa.

Preferably, in step (C), purging with ammonia gas is conducted until the phosgene concentration at the outlet of the phosgene synthesizing tower is below 1 ppm, preferably from 0.1 to 1 ppm, more preferably from 0.2 to 0.5 ppm.

Preferably, in step (B), ammonia gas is introduced into the phosgene synthesizing tower for building up pressure, such that the pressure in the phosgene synthesizing tower reaches from 0.11 to 5 MPa, more preferably from 0.2 to 4 MPa, more preferably from 0.5 to 3 MPa, more preferably from 0.7 to 2 MPa, e.g. 1 MPa, or reaches from 0.5 to 5 MPa, preferably from 1 to 3 MPa; Two operations including building up pressure and opening the outlet of the phosgene synthesizing tower are carried out once or several times repeatedly (i.e., opening the outlet of the phosgene synthesizing tower after building up pressure and then closing the outlet and building up pressure again), for example 3 to 10 times, preferably 4 to 8 times, preferably, the time for building up pressure each time is from 1 to 10 hours, preferably from 2 to 8 hours. In general, the shorter the time for building up pressure is, the more times the pressure is built up repeatedly, vice versa, the longer the time for building up pressure is, the less times the pressure is built up repeatedly. Building up pressure is to facilitate the ammonia gas to enter the pores of the activated carbon so as to fully react with the phosgene adsorbed in the pores of the activated carbon to remove the phosgene. The operations of repeatedly building up pressure and depressurization are also conducive to release the phosgene adsorbed in the pores of the activated carbon to react with the ammonia gas.

Preferably, in step (C), the flow of ammonia gas for purging the phosgene synthesizing tower is from 50 to 500 Nm$^3$/h, preferably from 80 to 150 Nm$^3$/h. The pressure of ammonia gas for purging is from 0.05 to 1.0 MPa, preferably from 0.102 to 0.3 MPa, more preferably from 0.15 to 0.25 MPa. The temperature of the ammonia gas is generally from 30 to 100° C., preferably from 40 to 80° C. It is preferred that the ammonia gas used for purging is substantially free of moisture (i.e. less than 20 ppm) or contains trace amounts of moisture, i.e. below 500 ppm, or from 20 to 500 ppm, preferably from 50 to 300 ppm of moisture. Phosgene is an acidic gas, ammonia gas is an alkaline gas, the two react quickly, and the reaction will be uneven if alkali liquor are selected for reaction with phosgene, and local acidity will cause equipment corrosion. In addition, ammonia gas and phosgene are reacted quickly, the reaction product is solid without moisture, which will not cause corrosion of equipment. Compared with phosgene, ammonia gas is less toxic. Therefore, after purging with nitrogen gas in the present invention, ammonia gas is used for purging.

Generally, in the step (C) of purging with ammonia gas, the time for purging with ammonia gas is from 1 to 10 days, preferably from 2 to 5 days.

Generally, the phosgene purged out from the phosgene synthesizing tower and excess ammonia gas are transferred to the phosgene decomposition tower and are decomposed by inorganic acids with the catalysis of the activated carbon. Preferably, the inorganic acids are hydrochloric acid, sulfuric acid, phosphoric acid, nitric acid, preferably hydrochloric acid or sulfuric acid, more preferably hydrochloric acid. It is preferable that the concentration of the inorganic acid was from 0.5 to 10% by mass, preferably from 1 to 5% by mass.

Preferably, the hot gas used in step D) is one of air, nitrogen gas, and CO$_2$, preferably air. The temperature of the hot gas is from 100 to 200° C., preferably from 120 to 180° C. The pressure of the hot gas is from 0.05 to 1.0 MPa, preferably from 0.102 to 0.3 MPa, preferably from 0.15 to 0.25 MPa. The flow rate of the hot gas is from 200 to 1000 Nm³/h, preferably from 300 to 800 Nm³/h.

Preferably, after the phosgene synthesizing tower is dried with the hot gas, the dew point measured therein is below −30° C., preferably below −40° C.

Generally, the catalyst in the phosgene synthesizing tower or the catalyst filled into the tubes of the phosgene synthesizing tower is preferably activated carbon, more preferably coke, coal-based charcoal, cocoanut charcoal, more preferably cocoanut charcoal.

In the present application, "building up pressure of the phosgene synthesizing tower with the ammonia gas", or "ammonia gas is introduced into the phosgene synthesizing tower for building up pressure" means that, in order to maintain the pressure inside the phosgene synthesizing tower higher than the atmospheric pressure, for example from 0.11 to 5 MPa, more preferably from 0.2 to 4 MPa, more preferably from 0.5 to 3 MPa, more preferably from 0.7 to 2 MPa, e.g. 1 MPa. The time for building up pressure each time or the time for maintaining pressure each time is generally from 30 min to 10 h, preferably from 1 h to 9 h, more preferably from 2 h to 8 h, more preferably from 2.5 h to 6 h. After building up the pressure, the outlet of the phosgene synthesizing tower is opened to discharge the ammonia gas. Two operations including building up pressure and opening the outlet of the phosgene synthesizing tower are carried out once or several times repeatedly (i.e., opening the outlet of the phosgene synthesizing tower after building up pressure and then closing the outlet and building up pressure again), for example 3 to 10 times, preferably 4 to 8 times.

In this application, "optional" means having or not. "Optionally" means carrying out or not.

Compared with the existing technology, the advantages of this method are as follows:

(1) the phosgene concentration at the outlet of the phosgene synthesizing tower can be ensured to be lower by first purging out a large amount of easily-desorbed phosgene in the phosgene synthesizing tower with nitrogen gas, then removing the remaining hardly-desorbed phosgene with the ammonia gas by reaction.

(2) By means of purging with nitrogen gas and then with ammonia gas, the ammonia gas can be directly reacted with the phosgene adsorbed in the pores of the activated carbon and thus more difficult to be desorbed in order to remove the latter, which greatly shortens the phosgene removal time of the phosgene synthesizing tower and makes the operation safer.

(3) The present invention solves the problem of longer phosgene removing time in the process of replacing the catalysts in the phosgene synthesizing tower at present, and lowers the risk of phosgene leakage in the phosgene purging process and improves the process safety.

BRIEF DESCRIPTION OF THE DRAWINGS

The FIGURE is a schematic view of a phosgene synthesizing tower apparatus used in Examples 1 to 4, wherein numerical reference 1 represents a phosgene synthesizing tower.

DETAILED DESCRIPTION OF THE INVENTION

The present invention will be further described with reference to the following examples, but the present invention is not limited thereto. The experimental methods not specified for the specific conditions in the following examples are generally in accordance with conventional conditions.

The phosgene concentration at the outlet of the phosgene synthesizing tower can be measured by an iodometric method known to those skilled in the art.

EXAMPLE 1

After feeding to the phosgene synthesizing tower was stopped, 100 Nm³/h of nitrogen gas was introduced from the bottom of the synthesizing tower, wherein the temperature of the nitrogen gas was 100° C., the moisture content in the nitrogen gas was 100 ppm, and the pressure of the nitrogen gas was 0.15 MPa. The nitrogen gas was continuously introduced for 2 days, and the phosgene concentration at the outlet of the phosgene synthesizing tower was measured as 0.45% (v/v) after purging. Ammonia gas was then introduced for purging. The ammonia gas was first introduced to build up the pressure, the phosgene synthesizing tower was built up pressure to 1 MPa and maintained at this pressure for 2 h, and then the outlet of the phosgene synthesizing tower was opened, and the process of building up pressure was repeated for 8 times as such. And then ammonia gas was continuously introduced, the flow of the ammonia gas was 80 Nm³/h, the temperature of the ammonia gas was 40° C., and the moisture content in the ammonia gas was 50 ppm. Purging with the ammonia gas was continued for 5 days, and the phosgene concentration at the outlet of the phosgene synthesizing tower was measured as 0.5 ppm. After purging, the phosgene was transferred to in a phosgene decomposition tower for decomposition, wherein the concentration of the inorganic acid was 1%, and the inorganic acid was hydrochloric acid. After purging with the ammonia gas, the tubes of the phosgene synthesizing tower were cleaned with a water gun, and the tubes were purged with hot air of 120° C. The hot air pressure was 0.15 MPa and the flow of the hot air was 300 Nm³/h, and the dew point of the synthesizing tower was measured as −40° C. The phosgene concentration at the outlet of the phosgene synthesizing tower and total purge time were shown in Table 1.

EXAMPLE 2

After feeding to the phosgene synthesizing tower was stopped, 200 Nm³/h of nitrogen gas was introduced from the bottom of the synthesizing tower, wherein the temperature of the nitrogen gas was 120° C., the moisture content in the nitrogen gas was 300 ppm, and the pressure of the nitrogen gas was 0.2 MPa. The nitrogen gas was continuously introduced for 3 days, and the phosgene concentration at the outlet of the phosgene synthesizing tower was measured as 0.3% (v/v) after purging. Ammonia gas was first introduced to build up the pressure, the phosgene synthesizing tower was built up pressure to 2 MPa and maintained at this pressure for 4 h, and then the outlet of the phosgene synthesizing tower was opened, and the process of building up pressure was repeated for 4 times as such. And then ammonia gas was continuously introduced, the flow of ammonia gas was 100 Nm³/h, and the temperature of the ammonia gas was 60° C. Purging with the ammonia gas was continued for 3 days, and the phosgene concentration at the out let of the phosgene synthesizing tower was measured as 0.4 ppm. After purging, the phosgene was decomposed in a phosgene decomposition tower, wherein the concentration of the inorganic acid was 2%, and the inorganic acid was hydrochloric acid. After purging with the ammonia gas, the tubes of the phosgene synthesizing tower were cleaned with a water gun, and the tubes were purged with hot nitrogen gas of 150° C. The pressure of the nitrogen gas was 0.25 MPa and the flow of the nitrogen gas was 500 $Nm^3/h$, and the dew point of the synthesizing tower was measured as −40° C. The phosgene concentration at the outlet of the phosgene synthesizing tower and total purge time were shown in Table 1.

EXAMPLE 3

After feeding to the phosgene synthesizing tower was stopped, 400 $Nm^3/h$ of nitrogen gas was introduced from the bottom of the synthesizing tower, wherein the temperature of the nitrogen gas was 150° C., the moisture content in the nitrogen gas was 200 ppm, and the pressure of the nitrogen gas was 0.25 MPa. The nitrogen gas was continuously introduced for 6 days, and the phosgene concentration at the outlet of the phosgene synthesizing tower was measured as 0.1% (v/v) after purging. And then Ammonia gas was introduced for purging, the ammonia gas was first introduced to build up the pressure, the phosgene synthesizing tower was built up pressure to 3 MPa and maintained at this pressure for 5 h, and then the outlet of the phosgene synthesizing tower was opened, and the process of building up pressure was repeated for 5 times as such. And then ammonia gas was continuously introduced for purging, the flow of the ammonia gas is 150 $Nm^3/h$, and the temperature of the ammonia gas was 80° C. Purging with the ammonia gas was conducted for 1 day, and the phosgene concentration at the out let of the phosgene synthesizing tower was measured as 0.2 ppm. After purging, the phosgene was decomposed in a phosgene decomposition tower, wherein the concentration of the inorganic acid was 5%, and the inorganic acid was hydrochloric acid. After purging with the ammonia gas, the tubes of the phosgene synthesizing tower were cleaned with a water gun, and the tubes were purged with hot air of 150° C. The pressure of the hot air was 0.2 MPa and the flow of the hot air was 800 $Nm^3/h$, and the dew point of the synthesizing tower was measured as −40° C. The phosgene concentration at the outlet of the phosgene synthesizing tower and total purge time were shown in Table 1.

EXAMPLE 4

After feeding to the phosgene synthesizing tower was stopped, 100 $Nm^3/h$ of nitrogen gas was introduced from the bottom of the synthesizing tower, wherein the temperature of the nitrogen gas was 100° C., the moisture content in the nitrogen gas was 100 ppm, the pressure of the nitrogen gas was 0.15 MPa. The nitrogen gas was continuously introduced for 2 days, and the phosgene concentration at the outlet of the phosgene synthesizing tower was measured as 0.45% (v/v) after purging. Ammonia gas was then continuously introduced, the flow of the ammonia gas was 80 $Nm^3/h$, the temperature of the ammonia gas was 40° C., and the moisture content in the ammonia gas was 50 ppm. Purging with the ammonia gas was conducted for 7 days, and the phosgene concentration at the out let of the phosgene synthesizing tower was measured as 0.5 ppm. After purging, the phosgene was decomposed in a phosgene decomposition tower, wherein the concentration of the inorganic acid was 1%, and the inorganic acid was hydrochloric acid. After purging with the ammonia gas, the tubes of phosgene synthesizing tower were cleaned with a water gun, and the tubes were purged with hot air of 120° C. The pressure of the hot air was 0.15 MPa and the flow of the hot air was 300 $Nm^3/h$, and the dew point of the synthesizing tower was measured as −40° C. The phosgene concentration at the outlet of the phosgene synthesizing tower and total purge time were shown in Table 1.

COMPARATIVE EXAMPLE 1

After feeding to the phosgene synthesizing tower was stopped, 500 $Nm^3/h$ of nitrogen gas was introduced from the bottom of the synthesizing tower, the temperature of the nitrogen gas was 120° C., the moisture content in the nitrogen gas was 100 ppm, and the pressure of the nitrogen gas was 0.5 MPa. The nitrogen gas was continuously introduced for 35 days, and the phosgene concentration at the outlet of the phosgene synthesizing tower was measured as 8.1 ppm after purging. The phosgene was decomposed in a phosgene decomposition tower after purging, wherein the concentration of the inorganic acid was 2%, and the inorganic acid was hydrochloric acid. After purging with the nitrogen gas, the tubes of the phosgene synthesizing tower tube were cleaned with a water gun, and the tubes were purged with hot nitrogen gas of 150° C. The dew point of the synthesizing tower was measured as −40° C., and the phosgene concentration at the outlet of the phosgene synthesizing tower and total purge time were shown in Table 1.

COMPARATIVE EXAMPLE 2

After feeding to the phosgene synthesizing tower was stopped, 500 $Nm^3/h$ of nitrogen gas was introduced from the bottom of the synthesizing tower, the temperature of the nitrogen gas was 150° C., the moisture content in the nitrogen gas was 100 ppm, the pressure of the nitrogen gas was 0.2 MPa. The nitrogen gas was continuously introduced for 30 days, and the phosgene concentration at the outlet of the phosgene synthesizing tower was measured as 10.2 ppm after purging. The phosgene was decomposed in a phosgene decomposition tower after purging, the concentration of the inorganic acid was 1%, and the inorganic acid was hydrochloric acid. After purging with the nitrogen gas, the tubes of the phosgene synthesizing tower were cleaned with a water gun, and the tubes were purged with hot nitrogen gas of 150° C. The dew point of the synthesizing tower was measured as −40° C., and the phosgene concentration at the outlet of the phosgene synthesizing tower and total purge time were shown in Table 1.

TABLE 1

Analysis results

| | Phosgene concentration after purging (ppm) | Nitrogen gas consumption ($Nm^3$) | Ammonia gas consumption ($Nm^3$) | Purging time (Days) |
|---|---|---|---|---|
| Example 1 | 0.5 | 4800 | 9600 | 7 |
| Example 2 | 0.4 | 14400 | 7200 | 6 |
| Example 3 | 0.2 | 57600 | 3600 | 7 |
| Comparative example 1 | 8.1 | 420000 | 0 | 35 |
| Comparative example 2 | 10.2 | 360000 | 0 | 30 |
| Example 4 | 0.5 | 4800 | 13440 | 10 |

The invention claimed is:

1. A method of quickly desorbing phosgene from a catalyst in a phosgene synthesizing tower having a bottom inlet and an outlet before the catalyst in the phosgene synthesizing tower is replaced, comprising:

(A) purging with nitrogen gas: after feeding of carbon monoxide and chlorine to the phosgene synthesizing tower is discontinued, nitrogen gas is introduced into the bottom of the phosgene synthesizing tower for purging, the phosgene in the phosgene synthesizing tower is purged to a phosgene decomposition tower until the phosgene concentration at the outlet of the phosgene synthesizing tower is measured as 0.05-0.5% (v/v), relative to the overall volume of gas; and (C) purging with ammonia gas: ammonia gas is continuously introduced into the bottom of the phosgene synthesizing tower for purging.

2. The method of claim 1, further comprising:

(D) replacing catalyst:
the catalyst is taken out from the phosgene synthesizing tower, and the fresh catalyst is loaded therein; or
when a tubular phosgene synthesizing tower is used, the catalyst is taken out from tubes of the phosgene synthesizing tower, and then the tubes of the phosgene synthesizing tower are rinsed with a water gun, and then dried with hot gas, and finally the fresh catalyst is filled into the tubes of the phosgene synthesizing tower.

3. The method of claim 1, wherein, in step (A), the temperature of the nitrogen gas for purging is from 80 to 160° C. and/or the content of moisture in the nitrogen gas is below 500 ppm.

4. The method of claim 1, wherein, in step (A), the flow of the nitrogen gas for purging is from 50 to 500 Nm3/h, the time for purging with nitrogen gas is from 1 to 10 days and the pressure for purging with nitrogen gas is from 0.05 to 1.0 MPa.

5. The method of claim 1, wherein, in step (C), purging with ammonia gas is conducted until the phosgene concentration at the outlet of the phosgene synthesizing tower is below 1 ppm.

6. The method of claim 1, wherein, in step (B), ammonia gas is introduced into the phosgene synthesizing tower for building up the pressure, such that the pressure in the phosgene synthesizing tower reaches from 0.11 to 5 MPa; and/or, two operations including building up the pressure and opening the outlet of the phosgene synthesizing tower are repeated 3 to 10 times.

7. The method of claim 1, wherein, in step (C) of purging with ammonia gas, the flow of the ammonia gas for purging the phosgene synthesizing tower is from 50 to 200 Nm3/h, and/or the pressure of the ammonia gas is from 0.05 to 1.0 MPa, and/or the temperature of the ammonia gas is from 30 to 100° C.

8. The method of claim 1, wherein, in the step (C) of purging with ammonia gas, the time for purging with ammonia gas is from 1 to 10 days.

9. The method of claim 1, wherein, the phosgene purged out by the phosgene synthesizing tower and excess ammonia gas are transferred to a phosgene decomposition tower and are decomposed by inorganic acids with the catalysis of an activated carbon.

10. The method of claim 8, further comprising adding inorganic acids, wherein the inorganic acids are hydrochloric acid, sulfuric acid, phosphoric acid, and nitric acid.

11. The method of claim 9, wherein the concentration of the inorganic acids is from 0.5 to 10% by mass.

12. The method of claim 2, wherein the hot gas used in step (D) is one of air, nitrogen gas, and CO2, and/or the temperature of the hot gas is from 100 to 200° C., and/or the pressure of the hot gas is from 0.05 to 1.0 MPa, and/or the flow of the hot gas is from 200 to 1000 Nm3/h.

13. The method of claim 2, wherein, after the phosgene synthesizing tower is dried with the hot gas, the dew point measured therein is below −30° C.

14. The method of claim 1, wherein the catalyst in the phosgene synthesizing tower or the catalyst filled into the tubes of the phosgene synthesizing tower is activated carbon.

15. The method of claim 1, further comprising:

(B) building the pressure: phosgene synthesizing tower is closed, ammonia gas in introduced into the bottom of the phosgene synthesizing tower to build up pressure in the phosgene synthesizing tower, and then the outlet of the phosgene synthesizing tower is opened to discharge gas from the phosgene synthesizing tower, wherein two operations including building up pressure and opening the outlet of the phosgene synthesizing tower are carried out once or several times repeatedly, wherein step (B) is performed after step (A) and prior to step (C).

* * * * *